US011185279B2

(12) United States Patent
Talgorn et al.

(10) Patent No.: US 11,185,279 B2
(45) Date of Patent: Nov. 30, 2021

(54) DETECTING ERYTHEMA CAUSED BY WEARABLE DEVICES

(71) Applicant: KONINKLIJKE PHILIPS N.V., Eindhoven (NL)

(72) Inventors: Elise Claude Valentine Talgorn, Eindhoven (NL); Willem Verkruijsse, Veldhoven (NL); Lieven Adriaenssen, Vilvoorde (BE)

(73) Assignee: Koninklijke Philips N.V., Eindhoven (NL)

(*) Notice: Subject to any disclaimer, the term of this patent is extended or adjusted under 35 U.S.C. 154(b) by 82 days.

(21) Appl. No.: 16/478,682

(22) PCT Filed: Jan. 18, 2018

(86) PCT No.: PCT/EP2018/051192
§ 371 (c)(1),
(2) Date: Jul. 17, 2019

(87) PCT Pub. No.: WO2018/134298
PCT Pub. Date: Jul. 26, 2018

(65) Prior Publication Data
US 2019/0388022 A1 Dec. 26, 2019

(30) Foreign Application Priority Data
Jan. 18, 2017 (EP) .................................... 17152001

(51) Int. Cl.
*A61B 5/00* (2006.01)
*A61B 5/0205* (2006.01)
(Continued)

(52) U.S. Cl.
CPC ............ *A61B 5/445* (2013.01); *A61B 5/0082* (2013.01); *A61B 5/02055* (2013.01);
(Continued)

(58) Field of Classification Search
CPC ... A61B 5/445; A61B 5/0082; A61B 5/02055; A61B 5/4839; A61B 5/7246;
(Continued)

(56) References Cited

U.S. PATENT DOCUMENTS

| 10,426,360 B2 * | 10/2019 | Nousiainen | ........ A61B 5/02427 |
| 2003/0135098 A1 * | 7/2003 | Lockhart | ................ A61B 5/411 |
| | | | 600/310 |

(Continued)

FOREIGN PATENT DOCUMENTS

| CN | 101347328 A | * | 1/2009 | ........... A61B 5/1032 |
| WO | WO-2011159148 A2 | * | 12/2011 | ........... A61B 5/0059 |

(Continued)

OTHER PUBLICATIONS

"Pearse, A.D., et al., Portable eythema meter and its application to use in human skin, Oct. 5, 1989, International Journal of Cosmetic Science, 12, 63-70" (Year: 1990).*

(Continued)

*Primary Examiner* — Jennifer Pitrak McDonald
*Assistant Examiner* — Michael T. Holtzclaw

(57) ABSTRACT

Techniques are described for detecting erythema caused by wearable devices. In various embodiments, a wearable device may include light source(s) to emit light at multiple wavelengths; light sensor(s) to receive light reflected from tissue of an individual that wears the wearable device; and logic configured to: operate the light source(s) to emit light at multiple wavelengths; receive a signal generated by the light sensor(s), wherein the signal is generated by the light sensor(s) in response to detection of light reflected from the tissue; analyze the signal to determine a first metric from a first wavelength of the light reflected from a first depth of the tissue and a second metric from a second wavelength of the light reflected from a second depth of the tissue; identify a (Continued)

correlation between the first and second metrics; and provide output indicative of tissue erythema based on the correlation.

15 Claims, 4 Drawing Sheets

(51) Int. Cl.
*A61M 35/00* (2006.01)
*A61B 5/024* (2006.01)

(52) U.S. Cl.
CPC .......... *A61B 5/4839* (2013.01); *A61B 5/7246* (2013.01); *A61B 5/7264* (2013.01); *A61M 35/003* (2013.01); *A61B 5/02438* (2013.01)

(58) Field of Classification Search
CPC ... A61B 5/7264; A61B 5/02438; A61B 5/681; A61B 5/6802; A61B 5/0059; A61M 35/003
See application file for complete search history.

(56) References Cited

U.S. PATENT DOCUMENTS

| | | | |
|---|---|---|---|
| 2008/0275327 A1* | 11/2008 | Faarbaek | A61B 5/411 600/382 |
| 2009/0326354 A1* | 12/2009 | Mao | A61B 5/14532 600/344 |
| 2010/0016733 A1* | 1/2010 | Smith | A61B 5/0295 600/483 |
| 2010/0185064 A1* | 7/2010 | Bandic | A61B 5/415 600/306 |
| 2013/0041235 A1* | 2/2013 | Rogers | A61B 5/1107 600/306 |
| 2013/0131762 A1* | 5/2013 | Oversluizen | A61N 5/0616 607/90 |
| 2015/0208964 A1* | 7/2015 | Addison | A61B 5/14551 600/324 |
| 2016/0080665 A1* | 3/2016 | Barnes | A61B 5/0064 348/77 |

FOREIGN PATENT DOCUMENTS

| | | |
|---|---|---|
| WO | 2015150106 A1 | 10/2015 |
| WO | 2016096591 A1 | 6/2016 |
| WO | WO-2016096591 A1 * | 6/2016 ........... A61B 5/0059 |

OTHER PUBLICATIONS

"Diffey, B.L., et al. A portable erythema instrument for quantifying erythema induced by ultraviolet radiation, May 5, 1984, British Journal of Dermatology, III, 663-672" (Year: 1984).*

"Earley, Elizabeth, What's the difference between AC and DC?, Sep. 17, 2013, MIT School of Engineering—Ask an Engineer" (Year: 2013).*

Pearse, A. D. et al., "Portable erythema meter and its application to use in human skin", International Journal of Cosmetic Science, 12, 63-70, 1990.

International Search Report and Written Opinion, International Application No. PCT/EP2018/051192, dated Apr. 26, 2018.

Baek, J. et al., "Flexible polymeric dry electrodes for the long-term monitoring of ECG", Sensors and Actuators A 143 (2008) 423-429.

Chen, Y. et al., "Soft, Comfortable Polymer Dry Electrodes for High Quality ECG and EEG Recording", Sensors 2014, 14(12), 23758-23780; https://doi.org/10.3390/s141223758.

"DexCom Adhesive Irritation & Allergy", https://thisiscaleb.com/2011/02/24/dexcom-adhesive-irritation-allergy/, Feb. 2011.

* cited by examiner

DETECTING ERYTHEMA CAUSED BY WEARABLE DEVICES

This application is the U.S. National Phase application under 35 U.S.C. § 371 of International Application No. PCT/EP2018/051192, filed on 18 Jan. 2018, which claims the benefit of European Application Serial No. 17152001.8, filed 18 Jan. 2017. These applications are hereby incorporated by reference herein.

TECHNICAL FIELD

The present disclosure is directed generally to health care. More particularly, but not exclusively, various methods and apparatus disclosed herein relate to detecting erythema (tissue irritation) caused by wearable devices.

BACKGROUND

Wearable devices that measure physiological parameters and/or administer various types of treatment (e.g., medicines, heat, electricity, etc.) are becoming more common in the health care industry. These wearable devices may take various forms, such as patches, tattoo-like devices, and so forth. In addition, wearable electronics such as smart watches, smart belts, etc., that are capable of measuring various physiological parameters are also becoming ubiquitous. However, wearable devices may cause underlying superficial erythema (skin irritation) in various circumstances, such as after prolonged use. Skin irritation below patches may be related in some cases to maceration, i.e. prolonged exposition of the skin to moisture due to sweat that accumulates under the wearable device. Erythema may cause discomfort to the user and possibly damage to the skin. In order to ensure adherence to a wearable device regimen, particularly in the home monitoring context, it would be beneficial to detect and/or limit erythema. Currently, treating erythema may require repositioning, replacement, and/or removal of the wearable device, e.g., to treat the underlying skin. These treatments may impose additional workload on medical personnel and/or on the user, and may increase costs.

SUMMARY

The present disclosure is directed to methods and apparatus for detecting tissue irritation (i.e. erythema) caused by wearable devices. In various embodiments, a wearable device such as a patch or wearable smart electronic (e.g., watch, band, belt, cuff, etc.) may be configured with one or more light sources (e.g., light emitting diodes, or "LEDs") and one or more light sensors (e.g., photosensors such as photodiodes, phototransistors, reverse-biased LEDs, etc.). The light sources may emit light (e.g., photoplethysmogram or "PPG" light) towards the underlying tissue at various wavelengths. This emitted light may enter the tissue, and at least some of the light may be reflected back towards the light sensors. Reflected light detected by the light sensors may be analyzed, e.g., at various wavelengths and/or using various components of the reflected light, to identify multiple signals or metrics indicative of erythema. In some embodiments, one or more signals/metrics may be correlated with other signals/metrics to distinguish superficial erythema caused by the wearable device from other phenomena, such as heightened stress, moisture buildup at the tissue-wearable device interface (which may be mistaken for skin irritation if analyzed alone), exercise, climate, and so forth.

Generally, in one aspect, a wearable device may include: one or more light sources to emit light at multiple wavelengths; one or more light sensors to receive light emitted by the one or more light sources that is reflected from tissue of an individual that wears the wearable device; and logic operably coupled with the one or more light sources and the one or more light sensors. The logic may be configured to: operate the one or more light sources to emit light at two or more wavelengths; receive a signal generated by the one or more light sensors, wherein the signal is generated by the one or more light sensors in response to detection, by the one or more light sensors, of light reflected from the tissue of the individual; analyze the signal to determine, from a first wavelength of the light reflected from a first depth of the tissue of the individual, a first metric; analyze the signal to determine, from a second wavelength of the light reflected from a second depth of the tissue of the individual, a second metric, wherein the second depth is different from the first depth; identify a correlation between the first metric and the second metric; and provide output indicative of tissue erythema based at least in part on the correlation.

In various embodiments, the first metric may include an amplitude of a DC component of the light reflected from the first depth at the first wavelength. In various embodiments, the first wavelength may include blue or green-yellow light. In various embodiments, the second metric may include an amplitude of the light reflected from the second depth. In various embodiments, the second wavelength may include red or infrared light.

In various embodiments, the second metric may include an amplitude of an AC component of the light reflected from the second depth at the second wavelength. In various embodiments, the correlation may be detected when a first amplitude of the light reflected from the first depth at the first wavelength satisfies a first threshold and a second amplitude of the light reflected from the second depth at the second wavelength satisfies a second threshold.

In various embodiments, the device may further include a temperature sensor operably coupled with the logic. The logic may be further configured to detect another correlation between a temperature of the tissue detected by the temperature sensor and one or more both of the first and second metrics. The output indicative of tissue erythema may be provided further based at least in part on the another correlation.

In various embodiments, the logic may be further configured to detect another correlation between a detected heart rate of the individual and one or both of the first and second metrics. The output indicative of tissue erythema may be provided further based at least in part on the another correlation.

In various embodiments, the device may further include a flexible substrate that is affixable to the tissue of the individual. The flexible substrate may include a plurality of electrically-activated pores. The logic may be further configured to electrically activate the pores to increase air flow to a portion of the tissue beneath the flexible substrate based at least in part on the correlation.

In various embodiments, the device may include a substrate that is positionable against the tissue of the individual. The substrate may include a reservoir containing one or more skin treatment chemicals. The logic may be further configured to provide the one or more skin treatment chemicals to the tissue beneath the substrate based at least in part on the correlation.

In another aspect, a method may include: operating one or more light sources of a wearable device worn by a user to emit light at two or more wavelengths; receiving, at logic of the wearable device, a signal generated by one or more light sensors of the wearable device, wherein the signal is generated by the one or more light sensors in response to detection, by the one or more light sensors, of light reflected from the tissue of the individual; analyzing, by the logic, the signal to determine, from a first wavelength of the light reflected from a first depth of the tissue of the individual, a first metric; analyzing, by the logic, the signal to determine, from a second wavelength of the light reflected from a second depth of the tissue of the individual, a second metric, wherein the second depth is different from the first depth; identifying, by the logic, a correlation between the first metric and the second metric; and providing, by the logic, output indicative of tissue erythema based at least in part on the correlation.

Additionally or alternatively, wearable device may include: one or more LEDs to emit light at multiple wavelengths; one or more photosensors to receive light emitted by the one or more LEDs that is reflected from tissue of an individual that wears the wearable device; and logic operably coupled with the one or more LEDs and the one or more photosensors. The logic may be configured to: operate the one or more LEDs to emit light; receive a signal generated by the one or more photosensors, wherein the signal is generated by the one or more photosensors in response to detection, by the one or more photosensors, of light reflected from the tissue of the individual; analyze the signal to determine, from a DC component of the light reflected from the tissue of the individual, a first metric; analyze the signal to determine, from an AC component of the light reflected from the tissue of the individual, a second metric; identify a correlation between the first metric and the second metric; and provide output indicative of tissue erythema based at least in part on the correlation.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

DETAILED DESCRIPTION

Wearable devices that measure physiological parameters and/or administer various types of treatment (e.g., medicines, heat, electricity, etc.) are becoming more common in the health care industry. These wearable devices may take various forms, such as patches, tattoo-like devices, and so forth. In addition, wearable electronics such as smart watches, smart belts, etc., that are capable of measuring various physiological parameters are also becoming ubiquitous. However, wearable devices may cause underlying superficial erythema (skin irritation) in various circumstances, such as after prolonged use. Skin irritation below patches may be related in some cases to maceration, i.e. prolonged exposition of the skin to moisture due to sweat that accumulates under the wearable device. Erythema may cause discomfort to the user and possibly damage to the skin. Currently, treating erythema may require repositioning, replacement, and/or removal of the wearable device, e.g., to treat the underlying skin. These treatments may impose additional workload on medical personnel and/or on the user, and may increase costs.

In order to ensure adherence to a wearable device regimen, particularly in the home monitoring context, it would be beneficial to detect and/or limit erythema. More generally, Applicants have recognized and appreciated that it would be beneficial to notify users of wearable devices (and/or medical personnel) when erythema (or onset of erythema) is detected, so that remedial action can be taken. In view of the foregoing, various embodiments and implementations of the present disclosure are directed to wearable devices configured to detect erythema in underlying tissue.

In PPG nomenclature, a PPG waveform may include so-called direct current ("DC") and alternating current ("AC") components. The DC component of the PPG waveform may correspond to light reflected from tissue at or near a surface, and may have an amplitude that depends on factors such as the tissue structure and/or average blood volume of both arterial and venous blood. The AC component of the PPG waveform may demonstrate changes in blood volume that occur between systolic and diastolic phases of the cardiac cycle.

Figure 1:
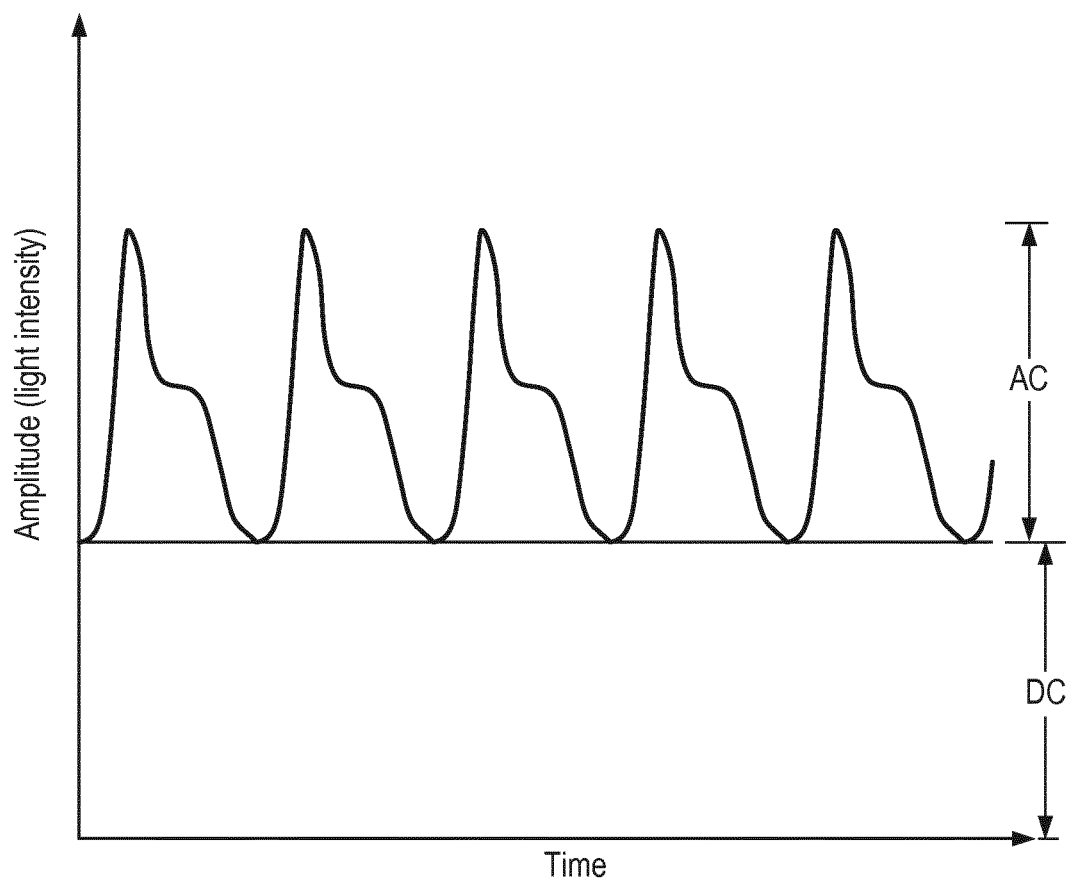
FIG. 1 illustrates an example chart showing AC and DC components of a PPG waveform.

FIG. 1 schematically depicts an example PPG waveform that shows both AC and DC components of light reflected from living tissue. The DC component of the PPG waveform represents average blood volume. The AC component of the PPG waveform represents changes in blood volume that occur between systolic and diastolic phases of the cardiac cycle. A reduced amplitude of the DC component may be indicative of skin redness. However, the DC component amplitude may also be highly dependent on other factors, such as a distance between the tissue and the light source(s), a distance between the tissue and the light sensor(s), and/or a moisture level at the interface between the wearable device and the tissue surface. Light scattering is generally wavelength-dependent (larger scattering for shorter wavelengths), so a change in the scattering properties of the interface between the wearable device and the tissue surface may cause a decrease in the DC component amplitude for relatively short wavelengths. Thus, analyzing the DC component amplitude alone may result in a false positive for tissue erythema.

Accordingly, in various embodiments described herein, both AC and DC components of light emitted by wearable devices (and reflected from or transmitted through tissue) may be used (in conjunction with other metrics in some embodiments) to detect tissue erythema more accurately. For example, in some embodiments, the amplitude of the AC component may be used as a metric for vasodilation of blood vessels beneath the tissue surface. Rather than basing a determination of tissue erythema solely on a reduction in amplitude of the DC component from a DC baseline (which as noted above may be caused by phenomena other than erythema), in various embodiments, a change (e.g., an increase) in the amplitude of the AC component from an AC baseline may be correlated with the change in amplitude of the DC component to detect tissue erythema.

Figure 2A:
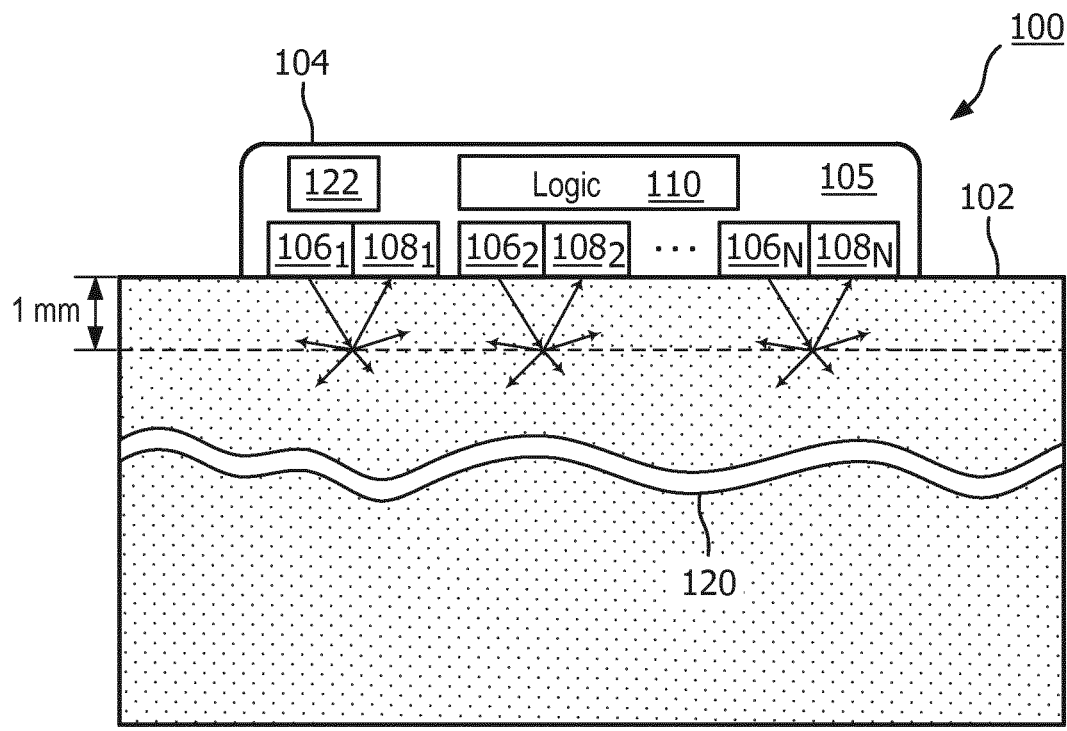
FIGS. 2A and 2B depict example embodiments of the present disclosure.

FIG. 2A depicts, in cross section, tissue 100 of a user (e.g., a patient or another individual) with an outer surface 102 (e.g., skin surface). A wearable device 104 may include a substrate 105 (which may or may not be flexible) that is affixed to outer surface 102 of tissue 100 and includes one or more light sources $106_{1-N}$ (e.g., LEDs) and light sensors $108_{1-N}$ (e.g., photosensors such as photodiodes, phototransistors, and/or reverse-biased LEDs). In some embodiments, a light source 106 and a light sensor 108 may form a unitary unit (e.g., an LED used both to emit light and detect reflected light). In some embodiments, light emitted by light sources 106 may be similar to light used during PPG.

In various embodiments, logic 110 may be operably coupled with light sources 106 and light sensors 108. Logic 110 may take various forms, such as one or more processors configured to execute instructions stored in memory (not depicted), a field programmable gate array ("FPGA"), an application specific integrated circuit ("ASIC"), and so forth. In some embodiments, logic 110 may also be operably coupled with one or more output devices 122 integral with wearable device 104. Output devices 122 may come in various forms, such as one or more LEDs that are visible to the naked eye, speakers, haptic feedback mechanisms (e.g., to cause vibration), wireless transmitters/transceivers that utilize various wireless technologies (e.g., low energy Bluetooth, Wi-Fi, RFID, EnOcean, ZigBee, Z-Wave, etc.), and so forth.

While not depicted in FIG. 2A, in some embodiments, wearable device 104 may include one or more physiological sensors operably coupled with logic 110 that are configured to measure various physiological parameters of the user, including but not limited to heart rate, sweat, temperature, SpO2, one or more biomarkers, glucose, and so forth. Additionally or alternatively, in various embodiments, wearable device 104 may include one or more mechanisms for applying treatment to the user, such as one or more reservoirs containing one or more chemicals (e.g., topical medicines, other medicines, insulin, etc.) that may be provided to tissue 100, and/or other components such as electrodes, heating/cooling elements, and so forth.

As indicated by the arrows, one or more light sources 106 may be configured to emit light towards tissue 100. The emitted light may, upon penetrating tissue 100, scatter in various ways. At least some of the scattered light (e.g., the light that is reflected back towards surface 102) may be detected by one or more light sensors 108. The amount of scattering of the emitted light may depend on a variety of factors, including a wavelength at which the light is emitted. For example, the shorter the wavelength, the greater the scattering. Additionally, the depth that the emitted light penetrates into tissue 100 may be wavelength dependent. The shorter the wavelength, the less deep the light penetrates. For example blue light tends to penetrate less than 1 mm. Red light tends to penetrate tissue 100 to about 2 mm. Near infrared light may penetrate tissue 100 as much as 4 mm.

In FIG. 2A, light sources 106 are emitting light solely in the blue or green-yellow wavelength (or "spectrum"). Consequently, the light does not penetrate further than about 1 mm into tissue 100. The reflected light that is captured by one or more light sensors 108—which may correspond to a DC component of the PPG waveform—is likewise in the blue and/or green-yellow spectrum. This light that is reflected from depths of less than 1 mm beneath surface 102 may be indicative of color change to surface 102. For example, when the surface 102 beneath wearable device 104 becomes red, this color change may be detected by logic 110, e.g., by analyzing one or more attributes (e.g., amplitude) of signals produced by light sensors 108. However, such color change may be caused by phenomena other than erythema. For example, moisture may build up between wearable device 104 and surface 102, introducing artifacts into the reflected light that is detected by light sensors 108. Accordingly, if logic 110 solely uses blue and/or green-yellow light reflected from a depth of 1 mm or less to detect erythema, the aforementioned artifacts may result in false positives.

Figure 2B:
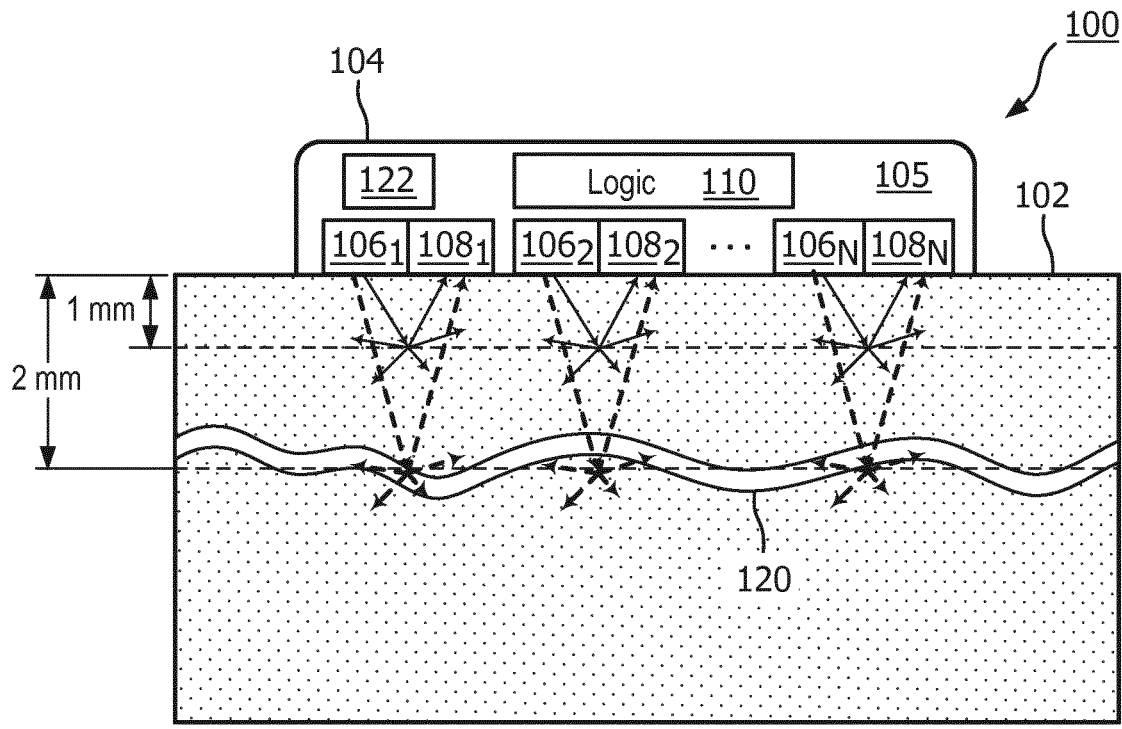

Accordingly, and as is depicted in FIG. 2B, in various embodiments, logic 110 may be configured to operate one or more light sources 106 to emit light at multiple wavelengths selected to penetrate tissue 100 at multiple different depths. Upon detecting the reflected light at the multiple wavelengths, one or more light sensors 108 may generate signals that may be analyzed by logic 110 to determine, based on multiple metrics, whether tissue erythema is present.

For example, in some embodiments, logic 110 may receive one or more signals generated by one or more light sensors 108. The one or more signals may be generated by one or more light sensors 108 in response to detection, by one or more light sensors 108, of light reflected from tissue 100. In various embodiments, logic 110 may analyze the signal(s) to determine, e.g., from a first wavelength of the light reflected from a first depth of tissue 100, a first metric. For example, in FIG. 2B, light emitted by light sources 106 includes a component at a first wavelength—indicated by the solid line arrows—that penetrates into tissue 100 to a first depth, which is less than 1 mm in this example. Thus, the first wavelength may be, for instance, blue, green, and/or yellow light. In various embodiments, the first metric may be an amplitude of a DC component in the first wavelength that is detected by light sensor(s) 108.

Likewise, logic 110 may analyze the signal(s) to determine, from a second wavelength of the light reflected from a second depth of tissue 100, a second metric. For example, in FIG. 2B, light emitted by light sources 106 includes a component at a second wavelength—indicated by the dashed arrows—that penetrates more deeply into tissue 100 to a second depth, which about 2 mm in this example. Thus, the second wavelength may be, for instance, red light. In various embodiments, the second metric may be an amplitude of an AC component of reflected light, e.g., in the second wavelength (or in some cases, any wavelength) that is detected by light sensor(s) 108.

In various embodiments, logic 110 may be configured to detect a correlation between the first metric and the second metric. Based at least in part on the correlation, logic 110 may provide output indicative of tissue erythema. For example, suppose the first metric indicates a reduced (e.g., from a baseline) DC amplitude, e.g., in the yellow-green spectrum. This reduced DC amplitude may indicate that redness is detected at or near surface 102. However, it is possible that the reduced DC amplitude may be caused by factors other than skin irritation, such as artifacts introduced by moisture build up between wearable device 104 and surface 102 of tissue 100.

Accordingly, the second metric may be compared to the first metric to determine whether there is a correlation (e.g., whether the second metric "corroborates" a preliminary determination of erythema based on the first metric). Suppose the second metric indicates an elevated (e.g., from a baseline) AC amplitude, e.g., in the red or infrared spectrum. This elevated AC amplitude may indicate vasodilation of blood vessel(s) 120 at approximately 2 mm depth or greater. Taking the first metric (reduced DC amplitude in the yellow-green spectrum) and the second metric (elevated AC amplitude in any spectrum may be used in some cases) together, logic 110 may infer that erythema is, in fact, present. By contrast, if the second metric indicated a baseline AC amplitude (i.e. no vasodilation), then the first metric indicating reduced DC amplitude may be ignored as a likely artifact.

Figure 3:
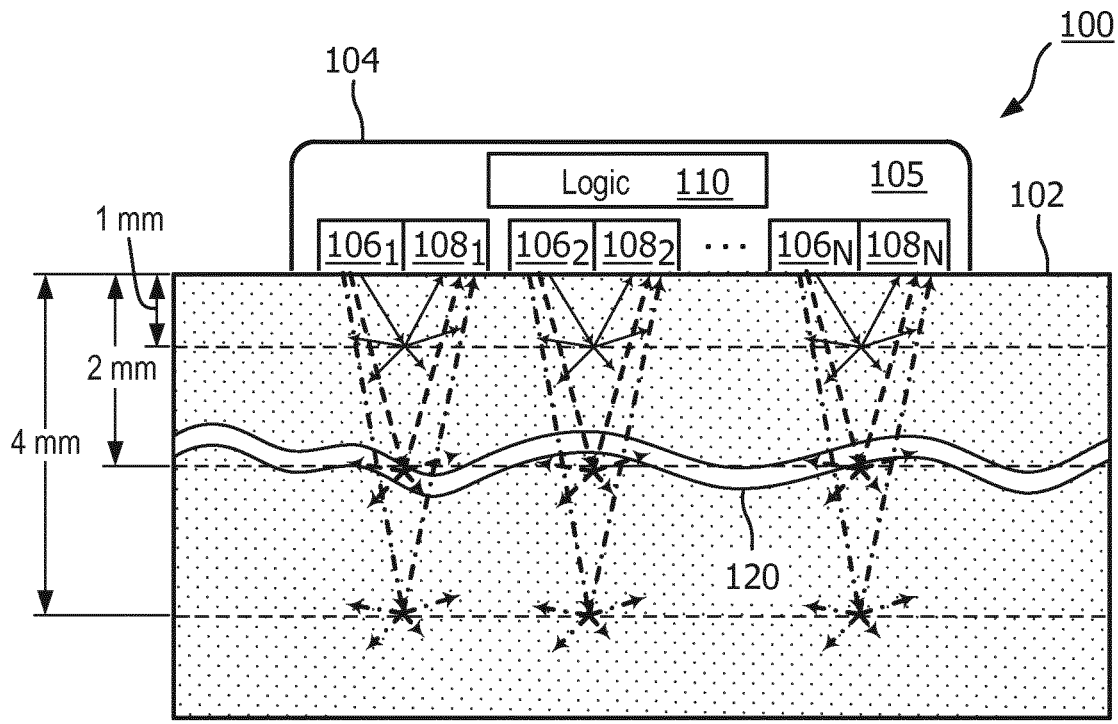
FIG. 3 depicts another example embodiment of the present disclosure.

In some embodiments, additional wavelengths of light may be used to determine whether detected skin redness is truly indicative of erythema or caused by other factors. Referring now to FIG. 3, a third wavelength of the light emitted by light sources 106—which is indicated by the dash-dot-dash arrows in FIG. 3—penetrates more deeply into tissue 100 than the first and second wavelengths, e.g., as far as 4 mm. Thus, the third wavelength may be, for instance, near infrared. In various embodiments, a third metric may be an AC component amplitude of reflected near infrared light that is detected by light sensors 108. Logic 110 may use such a third metric to corroborate and/or refute a determination made based on the first and/or second metrics.

In various embodiments, additional metrics may be employed in addition to or instead of those already described to detect erythema in tissue. These additional metrics may be provided by physiological sensors that are separate from, but in communication with, logic 110 (e.g., using wireless technology such as EnOcean, low power Bluetooth, RFID, etc.). For example, a user's smart watch may detect and provide the user's heart rate to a patch worn by the user. Additionally or alternatively, these other metrics may be provided by sensors that are integral with wearable device 104.

Figure 4:
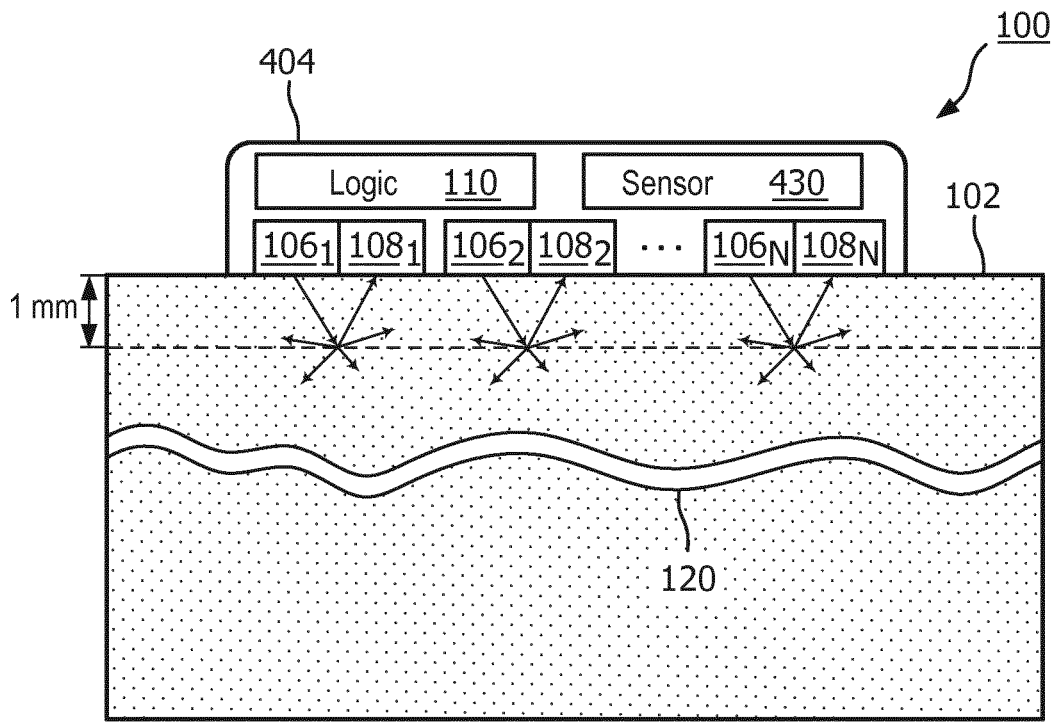
FIG. 4 depicts another example embodiment of the present disclosure.

In FIG. 4, for example, a wearable device 404 configured with selected aspects of the present disclosure (and including many of the same components as those embodiments depicted in prior figures) includes an integral physiological sensor 430. Physiological sensor 430 may be configured to detect one or more physiological parameters from tissue 100 other than skin redness. For example, physiological sensor 430 may be configured to detect heart rate. In some embodiments, one or more light sources 106 and/or light sensors 108 may be used to detect heart rate, e.g., using PPG techniques. In such embodiments, physiological sensor 430 and light sources 106/light sensors 108 may be combined. In other embodiments, other techniques may be used to detect heart rate, such as ultrasound, Doppler radar, electrocardiogram ("ECG"), etc.

In various embodiments, one or more additional metrics provided by physiological sensor(s) 430 may be correlated with the first and/or second metrics described above to increase a confidence of a finding of erythema (or to refute such a finding). For example, suppose that the first metric (e.g., DC component amplitude in green-yellow wavelength) suggests skin surface redness, and that the second metric (e.g., AC component amplitude) suggests vasodilation beneath the tissue surface. Taken together, the first and second metrics may be correlated to suggest tissue erythema. However, suppose additional metric(s) provided by physiological sensor(s) evidence other causes for the skin redness and/or vasodilation, such as increased heart rate, increased body temperature, and so forth. These additional metrics may be used to decrease a confidence in the finding of erythema based on the first and second metrics, and in some instances may be used to refute the finding of erythema altogether.

Suppose a user's detected heart rate is provided to logic 110. If the user's heart rate is elevated, logic 110 may infer that the user is stressed, exercising, or is in a particular climate (e.g., cold weather). Any of these factors may cause an increase in heart rate and/or skin temperature, which in turn may increase skin redness and/or vasodilation of blood vessels 120 beneath surface 102 of tissue 100. Accordingly, if logic 110 determines that the user's heart rate is elevated, logic 110 may, for instance, disregard a reduced amplitude in a DC component of green-yellow light reflected by the user's tissue (which suggests skin surface redness). Additionally or alternatively, in some embodiments, logic 110 may disregard an increased amplitude in an AC component of light reflected by the user's tissue, which in the absence of elevated heart rate might otherwise indicate erythema.

In addition to or instead of heart rate, physiological sensor 430 may be configured to detect other physiological parameters for which elevated measurements may or may not be associated with stress, exercise, or other factors, such as temperature (of the wearer and/or of the wearer's environment), sweat levels, blood pressure, and so forth. These other physiological parameters may be used to correlate or refute any preliminary determination of tissue irritation made by logic 110 based on, for instance, a DC component of reflected light in the green-yellow spectrum (as described above).

Figure 5:
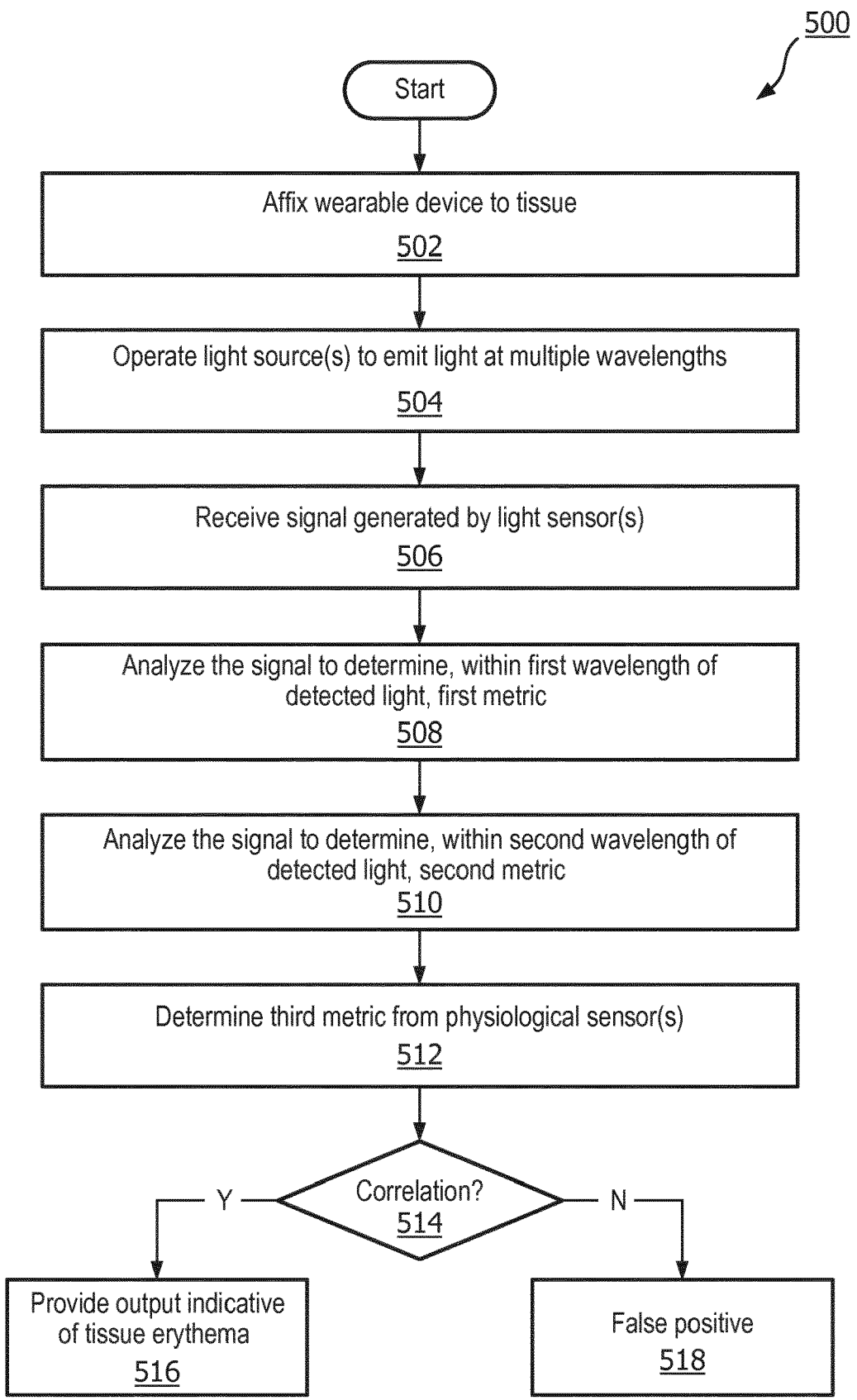
FIG. 5 depicts an example method in accordance with the present disclosure.

FIG. 5 depicts an example method 500 in accordance with various embodiments. While particular operations of method 500 are depicted in a particular order, this is not meant to be limiting. In various embodiments, one or more operations may be added, omitted, and/or reordered.

At block 502, a wearable device may be affixed to tissue. For example, a patch or tattoo-like device configured with selected aspects of the present disclosure may be adhered (e.g., using biocompatible adhesive) to a user's skin at various locations, such as the user's chest, forehead, appendages, abdomen, and so forth. Additionally or alternatively, a wearable computing device such as smart watch or smart band may be secured to the user's skin, e.g., by way of a belt or other similar mechanism.

At block 504, one or more light sources integral with the wearable device may be operated (e.g., by logic 110) to emit light at multiple wavelengths (e.g., across multiple spectrums). In some embodiments, light at multiple wavelengths may be emitted simultaneously. In other embodiments, light at different wavelengths may be emitted at different times, e.g., sequentially, alternating between two or more wavelengths, etc. The different wavelengths of light may penetrate to different depths of the underlying tissue, as described above.

At block 506, one or more signals generated by one or more light sensors that are integral with the wearable device may be received, e.g., at logic 110 or at logic of a remote computing device in wireless communication with a transmitter integral with the wearable device. At block 508, the signal(s) from the one or more light sensors may be analyzed to determine, from reflected light within a first (e.g., relatively short) wavelength, a first metric. At noted above, the first metric may include an amplitude of reflected light in one or more relatively short wavelength spectrums (e.g., green-yellow, blue, etc.). In some embodiments, the first metric may be a DC component of the reflected light in those one or more wavelengths.

As noted above, a reduced amplitude of a DC component of reflected light at relatively low wavelengths may be caused by redness in underlying tissue, but it also might be caused by an artifact such as moisture build up, a change in space between the light sensors and the skin surface, and so forth. Accordingly, at block 510, the signal(s) from the one or more light sensors may be analyzed to determine, from detected light within a second (e.g., relatively long) wavelength, a second metric. As noted above, the second metric may include an amplitude of reflected light, e.g., in one or more relatively long wavelength spectrums (e.g., red, near infrared, etc.). In some embodiments, the second metric may be an amplitude of an AC component of the reflected light. In some embodiments, at block 512 (which may be optional), a third metric (or additional metrics beyond a third metric) may be determined from one or more physiological sensors (e.g., 430). These sensors may be integral with the wearable device or remotely connected, e.g., by a wireless communication channel. These additional metrics may include, for instance, heart rate, temperature (in vivo or external), blood pressure, glucose levels, or any other parameter (physiological or otherwise) that may be used to corroborate or refute a preliminary determination of tissue erythema.

At block 514, it may be determined, e.g., by logic 110 integral with the wearable device or by logic of a remote computing device, whether there is correlation between at least the first and second metrics (and any additional metrics provided by physiological sensors at block 512, if available). For example, it may be determined whether a decrease in amplitude (e.g., from a baseline) of the DC component of reflected light in a relatively short wavelength is accompanied by a corresponding increase in amplitude of the AC of component of reflected light, e.g., in another relatively long wavelength. If additional metrics provided by physiological sensors at block 512 are available, then those metrics may likewise be correlated with the first and/or second metrics. For example, a heart rate metric indicating that the wearer's heart rate is not elevated (and therefore not likely exercising or stressed) may correlate changed AC and DC amplitudes at various wavelengths of reflected light.

If the answer at block 514 is yes, then method 500 may proceed to block 516. At block 516, output indicative of tissue erythema may be provided via one or more output devices (e.g., 122). For example, an LED or other visual output device integral with the wearable device may provide some sort of visual output (e.g., blinking, change in color, etc.). Additionally or alternatively an audio and/or haptic feedback device integral with the wearable device may provide audio and/or haptic feedback. In some embodiments in which output device 122 is a wireless transmitter, the output may include an outbound message that is transmitted wirelessly by the transmitter to a remote computing device, such as the wearer's smart phone or a computing device operated by medical personnel. Those remote computing devices may then respond by raising visual, audio, and/or haptic feedback. In some embodiments in which the wearable device is equipped with a reservoir, one or more chemicals stored in the reservoir (e.g., topical treatments) may be released and provided to the irritated area of the tissue, e.g., to heal or otherwise relieve (e.g., dry) the skin. Thus, a reservoir can be configured (or operable) to provide one or more skin treatment chemicals to the tissue beneath the substrate based at least in part on the correlation. In some embodiments, the logic 110 may be configured to control the reservoir to provide the one or more skin treatment chemicals to the tissue beneath the substrate based at least in part on the correlation. In some embodiments, the wearable device may include a structure that is operable to allow the skin beneath the wearable device to breathe. For instance, a patch may include pores that may be dilated (e.g., using chemicals, heat, electrical current, etc.) to increase air flow.

If the answer at block 514 is no, on the other hand, that may indicate that, for instance, the decrease in amplitude of the DC component of the reflected light was caused by phenomena other than skin redness, such as moisture buildup. In such case, no output may be raised, or different output may be provided to notify a user of the moisture buildup, or of sensor/device malfunction. For example, in some embodiments, if a threshold number of false positives are raised by the first and/or second metrics but contradicted by additional metrics provided by physiological sensors, then output may be provided indicating faulty light sources and/or sensors.

In some embodiments, wearable devices configured with selected aspects of the present disclosure may be equipped with mechanisms to facilitate light capture from tissue beneath the surface of the skin. For example, light guiding elements may be incorporated into some wearable devices to allow a larger area of tissue to be monitored. These light guiding elements may come in various forms, such as optical channels, crystals, lenses, and so forth. The light guiding elements may be configured, for instance, to capture light that is reflected from the tissue outside of a footprint of the wearable device and/or a footprint of an array of light sources. In some cases, one or more optical waveguides may be provided to guide reflected light that might not otherwise be captured towards light sensors. In some embodiments, one or more light guiding elements (and/or light sensors) may be disposed to guide and/or capture light that is scattered beneath an adhesive portion of a wearable patch configured with selected aspects of the present disclosure.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A wearable device, comprising:
   one or more light sources to emit light at multiple wavelengths;
   one or more light sensors to receive the light emitted by the one or more light sources that is reflected from tissue of an individual that wears the wearable device;
   a substrate that is affixable to the tissue of the individual, wherein the substrate comprises a plurality of pores that are dilatable; and
   logic operably coupled with the one or more light sources and the one or more light sensors, wherein the logic is configured to:
   operate the one or more light sources to emit the light at two or more wavelengths;
   receive a signal generated by the one or more light sensors, wherein the signal is generated by the one or more light sensors in response to detection, by the one or more light sensors, of the light that is reflected from the tissue of the individual;
   analyze the signal to determine, from a first wavelength of the light reflected from a first depth of the tissue of the individual, a first metric;
   analyze the signal to determine, from a second wavelength of the light reflected from a second depth of the tissue of the individual, a second metric, wherein the second depth is different from the first depth;
   identify a correlation between the first metric and the second metric;
   provide output indicative of tissue erythema caused by the wearable device based at least in part on the correlation; and
   activate the plurality of pores to dilate the plurality of pores to increase air flow to a portion of the tissue beneath the substrate based at least in part on the correlation.

2. The wearable device of claim 1, wherein the first metric comprises an amplitude of a DC component of the light reflected from the first depth at the first wavelength.

3. The wearable device of claim 2, wherein the first wavelength comprises blue or green-yellow light.

4. The wearable device of claim 1, wherein the second metric comprises an amplitude of the light reflected from the second depth.

5. The wearable device of claim 4, wherein the second wavelength comprises red or infrared light.

6. The wearable device of claim 1, wherein the second metric comprises an amplitude of an AC component of the light reflected from the second depth at the second wavelength.

7. The wearable device of claim 1, wherein the correlation is detected when a first amplitude of the light reflected from the first depth at the first wavelength satisfies a first threshold and a second amplitude of the light reflected from the second depth at the second wavelength satisfies a second threshold.

8. The wearable device of claim 1, further comprising a temperature sensor operably coupled with the logic, wherein the logic is further configured to detect another correlation between a temperature of the tissue detected by the temperature sensor and one or more of both of the first and second metrics, wherein the output indicative of tissue erythema is provided further based at least in part on the another correlation.

9. The wearable device of claim 1, wherein the logic is further configured to detect another correlation between a detected heart rate of the individual and one or both of the first and second metrics, wherein the output indicative of tissue erythema is provided further based at least in part on the another correlation.

10. The wearable device of claim 1, wherein the substrate is a flexible substrate, wherein the plurality of pores comprise a plurality of electrically-activated pores, and wherein the logic is further configured to electrically activate the plurality of electrically-activated pores to increase the air flow to the portion of the tissue beneath the flexible substrate based at least in part on the correlation.

11. The wearable device of claim 1, further comprising a substrate that is positionable against the tissue of the individual, wherein the substrate includes a reservoir containing one or more skin treatment chemicals, and wherein the reservoir is configured to provide the one or more skin treatment chemicals to the tissue beneath the substrate based at least in part on the correlation.

12. A method comprising:
operating, with logic of a wearable device, one or more light sources of the wearable device worn by an individual to emit light at two or more wavelengths;
receiving, at the logic, a signal generated by one or more light sensors of the wearable device, wherein the signal is generated by the one or more light sensors in response to detection, by the one or more light sensors, of the light that is reflected from tissue of the individual;
analyzing, by the logic, the signal to determine, from a first wavelength of the light reflected from a first depth of the tissue of the individual, a first metric;
analyzing, by the logic, the signal to determine, from a second wavelength of the light reflected from a second depth of the tissue of the individual, a second metric, wherein the second depth is different from the first depth;
identifying, by the logic, a correlation between the first metric and the second metric;
providing, by the logic, output indicative of tissue erythema caused by the wearable device based at least in part on the correlation; and
activating a plurality of pores to dilate the plurality of pores to increase air flow to a portion of the tissue beneath a substrate based at least in part on the correlation, wherein the substrate is affixed to the tissue of the individual and includes the plurality of pores.

13. The method of claim 12, wherein the first metric comprises an amplitude of a DC component of the light reflected from the first depth at the first wavelength.

14. The method of claim 12, wherein the second metric comprises an amplitude of an AC component of the light reflected from the second depth at the second wavelength.

15. A wearable device, comprising:
one or more LEDs to emit light at multiple wavelengths;
one or more photosensors to receive the light emitted by the one or more LEDs that is reflected from tissue of an individual that wears the wearable device;
logic operably coupled with the one or more LEDs and the one or more photosensors, wherein the logic is configured to:
operate the one or more LEDs to emit the light;
receive a signal generated by the one or more photosensors, wherein the signal is generated by the one or more photosensors in response to detection, by the one or more photosensors, of the light that is reflected from the tissue of the individual;
analyze the signal to determine, from a DC component of the light reflected from the tissue of the individual, a first metric;
analyze the signal to determine, from an AC component of the light reflected from the tissue of the individual, a second metric;
identify a correlation between the first metric and the second metric;
provide output indicative of tissue erythema caused by the wearable device based at least in part on the correlation; and
a substrate that is positionable against the tissue of the individual, wherein the substrate includes a reservoir containing one or more skin treatment chemicals, and wherein the reservoir is configured to provide the one or more skin treatment chemicals to the tissue beneath the substrate based at least in part on the correlation.

* * * * *